United States Patent [19]

Bauer

[11] Patent Number: 4,496,756
[45] Date of Patent: Jan. 29, 1985

[54] PROCESS FOR PREPARING AMINO ACID ESTERS

[75] Inventor: Dennis P. Bauer, Baton Rouge, La.

[73] Assignee: Ethyl Corporation, Richmond, Va.

[21] Appl. No.: 528,462

[22] Filed: Sep. 1, 1983

[51] Int. Cl.³ .............................................. C07C 101/02
[52] U.S. Cl. ...................................... 560/41; 560/125; 560/155
[58] Field of Search .......................... 560/41, 125, 155

[56] References Cited

U.S. PATENT DOCUMENTS

| | | | |
|---|---|---|---|
| 3,766,266 | 10/1973 | Wakamatsu et al. | 562/450 |
| 3,996,288 | 12/1976 | Yukata et al. | 562/445 X |
| 4,262,092 | 4/1981 | Bauer | 435/280 |
| 4,264,515 | 4/1981 | Stern et al. | 560/41 X |

FOREIGN PATENT DOCUMENTS 5737585  9/1979  Japan .

*Primary Examiner*—Bernard Helfin
*Attorney, Agent, or Firm*—Donald L. Johnson; John F. Sieberth; Patricia J. Hogan

[57] ABSTRACT

A enolizable organic compound, such as benzyl chloride, is reacted with an acid amide, an alcohol, carbon monoxide, and hydrogen in a homogeneous reaction mixture containing a cobalt carbonylation catalyst, an alkali metal alcoholate, and methyl isobutyl ketone so as to form an N-acylamino acid ester such as N-acetyl-D,L-phenylalanine methyl ester.

15 Claims, No Drawings

PROCESS FOR PREPARING AMINO ACID ESTERS

FIELD OF INVENTION

This invention relates to N-acylamino acid esters and more particularly to a process for preparing them.

BACKGROUND

Both D- and L-phenylalanines are useful materials that can be obtained in various ways. However, to obtain the optically pure isomers, it is generally necessary to resolve a racemic mixture of the D- and L-isomers or derivatives thereof, and a particularly attractive way of obtaining them is the enzymatic resolution of a mixture of an N-acyl-D-phenylalanine ester and an N-acyl-L-phenylalanine ester, as taught in U.S. Pat. No. 4,262,092 (Bauer). To get the starting material for this enzymatic resolution, it would obviously be desirable to develop an efficient, economical method of preparing the racemic ester mixture in a single step. It would also be desirable to develop such a process that would be generally useful in the preparation of N-acylamino acid esters.

It is known that N-acylamino acids can be prepared by a variety of techniques, e.g., by the one-step processes of U.S. Pat. Nos. 3,766,266 (Wakamatsu et al.) and 4,264,515 (Stern et al.) and Japanese Patent Publication No. SHO 57-37585 (Yukawa et al.), but each of the patentees indicates that esters would not easily be formed by their processes.

Wakamatsu et al. teach a means of preparing N-acylamino acids by reacting an aldehyde with carbon monoxide and an acid amide in the presence of a carbonylation catalyst and preferably in a solvent. In column 3, lines 42-46, they indicate that the corresponding esters may be prepared by including an alcohol in the solvent. However, they also teach that secondary reactions may occur to cause cyclization or condensation of the reaction product, and they do not provide any exemplification of an esterification reaction.

Stern et al. teach a process similar to the process of Wakamatsu et al. except for the substitution of an olefinic compound for the aldehyde of Wakamatsu et al. These patentees also indicate in column 4, lines 62-66, that the use of certain alcohol solvents permits esters to be formed in the reaction, but they additionally teach that the use of those solvents should be avoided because of their disadvantageous effect on the reaction rate.

Yukawa et al. disclose the preparation of N-acylamino acids, such as N-acylphenylalanine, in a single step wherein an organic halide, such as benzyl chloride, is reacted with carbon monoxide, hydrogen, and an acid amide in the presence of a base and a cobalt catalyst. Their teachings indicate that this reaction can be conducted in water or in a mixture of water and a water-soluble solvent but that the use of such homogeneous solvent media is not as advantageous as their use of a two-phase solvent system consisting of a combination of water and a water-insoluble solvent, such as a hydrocarbon, ketone, higher alcohol, ether, nitrile, or ester. In Practical Example 1, their only disclosure of forming an N-acylamino acid ester, they teach the one-step preparation of N-acetylphenylalanine followed by a second step of converting that product to the methyl ester.

SUMMARY OF INVENTION

An object of this invention is to provide a novel process for preparing N-acylamino acid esters.

Another object is to provide such a process that can be accomplished in a single step.

A further object is to provide such a process which is efficient and economical.

These and other objects are attained by reacting (1) an enolizable organic compound corresponding to the formula:

wherein X is a leaving group and R and R' are independently selected from hydrogen and innocuous substituents with (2) an acid amide, (3) an alcohol, (4) carbon monoxide, and (5) hydrogen in a homogeneous reaction mixture containing a cobalt carbonylation catalyst, an alkali metal alcoholate, and methyl isobutyl ketone so as to form an N-acylamino acid ester.

DETAILED DESCRIPTION

The enolizable organic compound used in the practice of the invention may be any compound corresponding to the formula CHRR'X, wherein X is a leaving group (e.g., halo or an optionally halogenated hydrocarbyloxy or hydrocarbylthio group in which hydrocarbyl may be alkyl, cycloalkyl, aryl, or aralkyl, etc.—preferably I, Br, or Cl) and R and R' are independently selected from hydrogen and innocuous substituents, i.e., substituents that do not prevent the reaction from occurring.

The particular enolizable compound preferred in any given instance varies, of course, with the particular N-acylamino acid ester desired. However, those that work best in the reaction are the compounds in which one of R and R' is hydrogen and the other is an innocuous hydrocarbon or substituted hydrocarbon group, e.g., an alkyl, cycloalkyl, aryl, alkaryl, or aralkyl group, optionally bearing one or more substituents, such as halo, nitro, etc., and generally containing about 1-20 carbons. Compounds containing a benzyl group work particularly well in the practice of the invention, and benzyl chloride is a preferred reactant when an N-acylphenylalanine ester is desired.

Acid amides utilizable in the process are generally compounds that correspond to the formula:

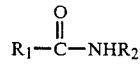

in which $R_1$ is hydrogen, hydrocarbyl, or substituted hydrocarbyl, e.g. an optionally substituted alkyl, cycloalkyl, aryl, aralkyl, or alkaryl group wherein any substituents are innocuous substituents, such as halo, nitro, etc.—preferably an alkyl group, e.g., an alkyl group containing about 1-10 carbons—and $R_2$ is hydrogen or an innocuous substituent, e.g., an alkyl group containing about 1-10 carbons. Usually the amide is an alkanamide containing about 1-10 carbons, preferably about 1-6 carbons, e.g., formamide, acetamide, propionamide, etc., or an N-alkylalkanamide, such as N-methylformamide, N-methylacetamide, etc.

As in the case of the enolizable organic compound, the particular amide reactant that is preferred in any given instance varies with the particular N-acylamino acid ester desired. However, since it is generally preferred to prepare an N-acetyl comound, the preferred amide is apt to be acetamide. The amount of amide employed is not critical but is usually in the range of about 1.0–10 mols per mol of the enolizable organic compound.

The alcohol employed in the process may be any alcohol capable of reacting with the other reactants to form an ester and may generally be described as a compound corresponding to the formula $R_3OH$, wherein $R_3$ is an optionally substituted alkyl, cycloalkyl, aryl, aralkyl, or alkaryl group—any substituents, of course, being innocuous substituents, such as fluoro, nitro, etc. However, it is usually an alkanol containing about 1–10 carbons, preferably 1–6 carbons, such as methanol, ethanol, n-propanol, isopropanol, or a butanol, pentanol, hexanol, etc.; and methanol is particularly preferred. This ingredient of the reaction mixture should be employed in at least the stoichiometric amount, i.e., at least one molar proportion per molar proportion of the enolizable organic compound, although the use of a deficit of the alcohol is not fatal to the practice of the invention. It is frequently desirable to employ the alcohol in excess, with the excess functioning to dilute the reaction mixture.

The carbon monoxide and hydrogen are generally supplied to the reaction mixture in admixture with one another, e.g., as water gas, and do not have to be pure in order for the reaction to occur. Although the mol ratio of carbon monoxide to hydrogen in the mixture is not critical, it is generally about 1:1, and the mixture is generally supplied in an amount sufficient to provide a stoichiometric excess of the carbon monoxide and hydrogen, i.e., more than one mol of hydrogen and more than two mols of carbon monoxide per mol of the enolizable group-containing organic compound. Ordinarily, the carbon monoxide/hydrogen mixture is used so as to provide a pressure of about 1450–8000 psig, frequently about 2500–3500 psig.

The cobalt carbonylation catalyst is usually dicobalt octacarbonyl, and it appears to function by decomposing to form $^-Co(CO)_4$, which reacts with the enolizable organic compound to displace the leaving group and then remains in the reaction product until displaced by the alcohol reactant. Therefore, it is preferably employed in an amount such as to supply at least about 0.5 molar proportion of cobalt catalyst per molar proportion of enolizable organic compound, although it is generally apt to be employed in such an amount as to supply about 0.1–10 molar proportion of cobalt catalyst per mol of enolizable organic compound. If desired, this cobalt catalyst may be employed in admixture with a co-catalyst, such as a phosphine, amine, or sulfur derivative, that is mixed with the cobalt catalyst prior to use in the reaction. Exemplary of such co-catalysts are tertiary phosphines, including aromatic and aliphatic phosphines; tertiary and heterocyclic amines, such as pyridine; dimethyl sulfide, etc.

The alkali metal alcoholate is a base that is essential to the accomplishment of the reaction and is generally a salt of an alkali metal, such as sodium, lithium, etc., with an alcohol which generally corresponds to the alcohol component. The alcoholate is usually employed in an amount such as to provide about 0.1–10 mols of the alcoholate per mol of the enolizable organic compound.

Methyl isobutyl ketone is utilized as a solvent that can keep any cobalt/enolizable organic compound reaction product in solution. This component of the reaction mixture is employed in diluent amounts.

The temperature at which the reaction is conducted is not critical but is usually maintained at about 50°–200° C. until the reaction has been accomplished, generally for at least about 30 minutes. The reaction product can then be isolated by known techniques and, as indicated earlier, can subsequently be resolved to separate D- and L-isomers.

The following example is given to illustrate the invention and is not intended as a limitation thereof.

EXAMPLE

A suitable reaction vessel was charged with one molar proportion of benzyl chloride, about 1.4 molar proportions of acetamide, 0.75 molar proportion of sodium methoxide, about 0.1 molar proportion of dicobalt octacarbonyl, 5 molar proportions of methanol, and about 5 molar proportions of methyl isobutyl ketone. The reaction mixture was then pressurized to 2800 psig with a 1:1 mol ratio mixture of carbon monoxide and hydrogen, heated with stirring to 110° C., and held there for 30 minutes. After being cooled to ambient temperature, the mixture was concentrated to a viscous oil which was taken up in chloroform, filtered through alumina, and concentrated in vacuuo to provide a 48.8% yield of an oily solid which was identified by proton nmr as N-acetyl-D,L-phenylalanine methyl ester.

It is obvious that many variations may be made in the products and processes set forth above without departing from the spirit and scope of this invention.

I claim:

1. A process which comprises reacting (1) an enolizable organic compound corresponding to the formula:

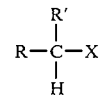

wherein X is a leaving group and R and R' are independently selected from hydrogen and innocuous substituents with (2) an acid amide, (3) an alcohol, (4) carbon monoxide, and (5) hydrogen in a homogeneous reaction mixture containing a cobalt carbonylation catalyst, an alkali metal alcoholate, and methyl isobutyl ketone so as to form an N-acylamino acid ester.

2. The process of claim 1 wherein X is a halogen selected from I, Br, and Cl.

3. The process of claim 1 wherein R or R' is hydrogen.

4. The process of claim 3 wherein CHRR' is an alkyl or substituted alkyl group.

5. The process of claim 3 wherein CHRR' is an aralkyl or substituted aralkyl group.

6. The process of claim 5 wherein CHRR' is benzyl.

7. The process of claim 1 wherein CHRR'X is benzyl chloride.

8. The process of claim 1 wherein the acid amide is an alkanamide containing 1–6 carbons.

9. The process of claim 8 wherein the alkanamide is acetamide.

10. The process of claim 1 wherein the alcohol is an alkanol containing 1–6 carbons.

11. The process of claim 10 wherein the alkanol is methanol.

12. The process of claim 1 wherein the alkali metal alcoholate is an alkali metal salt of an alkanol containing 1–6 carbons.

13. The process of claim 12 wherein the alkali metal alcoholate is sodium methoxide.

14. The process of claim 1 wherein the cobalt carbonylation catalyst is dicobalt octacarbonyl.

15. The process of claim 1 wherein benzyl chloride is reacted with acetamide, carbon monoxide, hydrogen, and methanol in the presence of dicobalt octacarbonyl, sodium methoxide, and methyl isobutyl ketone so as to form N-acetyl-D,L-phenylalanine methyl ester.

* * * * *